(12) United States Patent
Stolka et al.

(10) Patent No.: US 9,668,819 B2
(45) Date of Patent: *Jun. 6, 2017

(54) SURGICAL NEEDLE FOR A SURGICAL SYSTEM WITH OPTICAL RECOGNITION

(71) Applicant: Clear Guide Medical, LLC, Baltimore, MD (US)

(72) Inventors: Philipp Jakob Stolka, Baltimore, MD (US); Pezhman Foroughi, Cockeysville, MD (US); Matthew C. Rendina, Baltimore, MD (US); Gregory Donald Hager, Baltimore, MD (US); Emad Mikhail Boctor, Baltimore, MD (US)

(73) Assignee: CLEAR GUIDE MEDICAL, INC., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/508,223

(22) Filed: Oct. 7, 2014

(65) Prior Publication Data

US 2015/0148668 A1 May 28, 2015

Related U.S. Application Data

(63) Continuation of application No. 14/092,843, filed on Nov. 27, 2013, now Pat. No. 8,880,151.

(51) Int. Cl.
*A61B 6/00* (2006.01)
*A61B 19/00* (2006.01)
(Continued)

(52) U.S. Cl.
CPC ........ *A61B 19/5244* (2013.01); *A61B 1/3132* (2013.01); *A61B 5/0082* (2013.01);
(Continued)

(58) Field of Classification Search
CPC ... A61B 19/5244; A61B 90/361; A61B 90/30; A61B 34/20; A61B 1/3132;
(Continued)

(56) References Cited

U.S. PATENT DOCUMENTS 5,144,482 A   9/1992   Gould
6,019,724 A   2/2000   Gronningsaeter et al.
(Continued)

FOREIGN PATENT DOCUMENTS

EP   2289578 A1   3/2011
EP   2478855 A1   7/2012
(Continued)

OTHER PUBLICATIONS

Allaf et al., "Laparoscopic partial nephrectomy: evaluation of long-term oncological outcome," J Uro Sep. 2004;172(3):871-3.
(Continued)

*Primary Examiner* — Sanjay Cattungal
(74) *Attorney, Agent, or Firm* — Venable LLP; Henry J. Daley; Ilya Svetlov

(57) ABSTRACT

A system for image-guided surgery may include a visual imaging system, a medical tool comprising a shaft and a tip, wherein the shaft of the tool includes an optically detectable feature that allows a position of the tip to be determined, and a display configured to display a real-time representation of the medical tool including the position of the tip regardless of whether the tip is obstructed or visible.

19 Claims, 6 Drawing Sheets

(51) Int. Cl.
| | |
|---|---|
| A61B 10/04 | (2006.01) |
| A61B 5/00 | (2006.01) |
| A61B 8/00 | (2006.01) |
| A61B 8/08 | (2006.01) |
| A61M 5/42 | (2006.01) |
| A61M 5/46 | (2006.01) |
| A61B 1/313 | (2006.01) |
| A61B 34/20 | (2016.01) |
| A61B 90/30 | (2016.01) |
| A61B 90/00 | (2016.01) |
| A61B 5/06 | (2006.01) |
| A61B 17/34 | (2006.01) |

(52) U.S. Cl.
CPC .......... *A61B 8/0841* (2013.01); *A61B 8/4254* (2013.01); *A61B 8/464* (2013.01); *A61B 10/04* (2013.01); *A61B 34/20* (2016.02); *A61B 90/30* (2016.02); *A61B 90/361* (2016.02); *A61M 5/427* (2013.01); *A61M 5/46* (2013.01); *A61B 5/064* (2013.01); *A61B 8/4455* (2013.01); *A61B 2017/3413* (2013.01); *A61B 2034/2065* (2016.02); *A61B 2090/062* (2016.02); *A61B 2090/3937* (2016.02)

(58) Field of Classification Search
CPC ..... A61B 8/4254; A61B 5/0082; A61B 10/04; A61B 2090/062; A61B 2034/2065; A61B 2090/3937; A61B 2017/3413; A61B 5/064; A61B 8/4455; A61M 6188/0841
USPC .......... 600/437–469, 473–480, 424; 606/130
See application file for complete search history.

(56) References Cited

U.S. PATENT DOCUMENTS

| | | | |
|---|---|---|---|
| 6,234,969 | B1 | 5/2001 | Chaintreuil et al. |
| 6,491,702 | B2 | 12/2002 | Heilbrun et al. |
| 6,503,195 | B1 | 1/2003 | Keller et al. |
| 6,612,991 | B2 | 9/2003 | Sauer et al. |
| 6,711,429 | B1 | 3/2004 | Gilboa et al. |
| 7,103,212 | B2 | 9/2006 | Hager et al. |
| 7,171,255 | B2 | 1/2007 | Holupka et al. |
| 7,787,992 | B2 | 8/2010 | Pretlove et al. |
| 8,073,528 | B2 | 12/2011 | Zhao |
| 8,303,505 | B2 | 11/2012 | Webler et al. |
| 8,391,571 | B2 | 3/2013 | Cinquin et al. |
| 8,517,955 | B2 * | 8/2013 | Keast ................ A61B 10/0266 600/564 |
| 8,547,401 | B2 | 10/2013 | Mallinson et al. |
| 2002/0016533 | A1 | 2/2002 | Marchitto et al. |
| 2002/0077533 | A1 | 6/2002 | Bieger et al. |
| 2002/0115922 | A1 * | 8/2002 | Waner ................ A61B 5/0059 600/407 |
| 2003/0135115 | A1 | 7/2003 | Burdette et al. |
| 2003/0135119 | A1 | 7/2003 | Lee et al. |
| 2003/0158503 | A1 | 8/2003 | Matsumoto |
| 2004/0002657 | A1 | 1/2004 | Marian |
| 2004/0019274 | A1 | 1/2004 | Galloway |
| 2004/0019280 | A1 * | 1/2004 | Waner ................ A61B 5/0059 600/466 |
| 2004/0106869 | A1 | 6/2004 | Tepper |
| 2004/0152988 | A1 | 8/2004 | Weirich |
| 2004/0215072 | A1 | 10/2004 | Zhu |
| 2005/0085717 | A1 | 4/2005 | Shahidi |
| 2005/0182316 | A1 | 8/2005 | Burdette et al. |
| 2007/0073155 | A1 | 3/2007 | Park et al. |
| 2008/0188749 | A1 | 8/2008 | Rasche et al. |
| 2008/0266323 | A1 | 10/2008 | Biocca et al. |
| 2009/0292214 | A1 | 11/2009 | Ferren et al. |
| 2010/0168562 | A1 * | 7/2010 | Zhao ................ A61B 19/2203 600/426 |
| 2010/0168763 | A1 | 7/2010 | Zhao et al. |
| 2010/0298704 | A1 | 11/2010 | Pelissier et al. |
| 2010/0312141 | A1 * | 12/2010 | Keast ................ A61B 10/0266 600/567 |
| 2011/0009694 | A1 | 1/2011 | Schultz et al. |
| 2011/0166442 | A1 | 7/2011 | Sarvazyan |
| 2011/0166450 | A1 | 7/2011 | Peyrard et al. |
| 2011/0319759 | A1 | 12/2011 | Liu et al. |
| 2012/0140085 | A1 | 6/2012 | Gallinat et al. |
| 2012/0143049 | A1 | 6/2012 | Neubauer et al. |
| 2012/0253200 | A1 | 10/2012 | Stolka et al. |
| 2012/0289820 | A1 | 11/2012 | Rohling |
| 2012/0304128 | A1 | 11/2012 | Woo et al. |
| 2012/0313963 | A1 | 12/2012 | Chen-Quee et al. |
| 2013/0016185 | A1 | 1/2013 | Stolka et al. |
| 2013/0030286 | A1 | 1/2013 | Alouani et al. |
| 2013/0223702 | A1 * | 8/2013 | Holsing ............. A61B 19/5244 382/128 |
| 2013/0225942 | A1 * | 8/2013 | Holsing ............. A61B 19/5244 600/301 |
| 2013/0225943 | A1 * | 8/2013 | Holsing ............. A61B 19/5244 600/301 |
| 2013/0300829 | A1 * | 11/2013 | Urasaki ............. A61B 1/00009 348/45 |
| 2013/0331734 | A1 * | 12/2013 | Keast ................ A61B 10/0266 600/567 |

FOREIGN PATENT DOCUMENTS

| | | |
|---|---|---|
| WO | WO-2006/073869 A2 | 7/2006 |
| WO | WO-2007/059780 A1 | 5/2007 |
| WO | WO-2007113815 A2 | 10/2007 |
| WO | WO-2008/067072 A2 | 6/2008 |
| WO | WO-2008/098241 A1 | 8/2008 |
| WO | WO 2010-132985 | 11/2010 |
| WO | WO-2011/047467 A1 | 4/2011 |
| WO | WO-2013/055707 A1 | 4/2013 |

OTHER PUBLICATIONS

Benoist et al., "Complete response of colorectal liver metastases after chemotherapy: does it mean cure?" J Clin Oncol. Aug. 20, 2006;24(24):3939-45.

Berber et al., "Resection versus laparoscopic radiofrequency thermal ablation of solitary colorectal liver metastasis," J Gastrointest Surg. Nov. 2008;12(11):1967-72.

Bijol et al., "Evaluation of the nonneoplastic pathology in tumor nephrectomy specimens: predicting the risk of progressive renal failure," Am J Surg Pathol. May 2006;30(5):575-84.

Billings et al., "A hybrid surface/image based approach to facilitate ultrasound/CT registration," accepted SPIE Medical Imaging 2011.

Boctor et al., "Prostate brachytherapy seed localization using combined photoacoustic and ultrasound imaging," SPIE Medical Imaging 2010.

Boctor et al., "Robot-assisted 3D strain imaging for monitoring thermal ablation of liver," Annual congress of the Society of American Gastrointestinal Endoscopic Surgeons, pp. 240-241, 2005.

Boctor et al., "Ultrasound Monitoring of Tissue Ablation via Deformation Model and Shape Priors," International Conference on Medical Image Computing and Computer-Assisted Intervention, MICCAI 2006.

Bonadonna et al., "Primary chemotherapy in operable breast cancer: eight-year experience at the Milan Cancer Institute," SOJ Clin. Oncol. Jan. 1998;16(1):93-100.

Chagpar et al., "Accuracy of Physical Examination, Ultrasonography and Mammography in Predicting Residual Pathologic Tumor size in patients treated with neoadjuvant chemotherapy," Annals of surgery vol. 243, No. 2, Feb. 2006.

Chen et al., "A prospective randomized trial comparing percutaneous local ablative therapy and partial hepatectomy for small hepatocellular carcinoma," Ann Surg. Mar. 2006;243(3):321-8.

Coresh et al., "Prevalence of chronic kidney disease in the United States," JAMA Nov. 7, 2007;298(17):2038-47.

(56) References Cited

OTHER PUBLICATIONS

Fergany et al., "Long-term results of nephron sparing surgery for localized renal cell carcinoma: 10-year followup," J Uro Feb. 2000;163(2):442-5.
Foroughi et al., "Tracked Ultrasound Elastography (TrUE)," in Medical Image Computing and Computer Integrated surgery, 2010.
Goldberg et al., "Thermal ablation therapy for focal malignancy: a unified approach to underlying principles, techniques, and diagnostic imaging guidance," AJR Am J Roentgenol. Feb. 2000;174(2):323-31.
Goldsmith et al., "An Inertial-Optical Tracking System for Portable, Quantitative, 31) Ultrasound," 2008 IEEE Ultrasonics Symposium Proceedings, Beijing, China, Nov. 2-5, 2008.
Greenleaf et al., "Selected methods for imaging elastic properties of biological tissues," Annu Rev Biomed Eng. 2003;5:57-78.
Gruenberger et al., "Importance of response to neoadjuvant chemotherapy in potentially curable colorectal cancer liver metastases," BMC Cancer. Apr. 25, 2008;8:120.
Hafez et al., "Nephron sparing surgery for localized renal cell carcinoma: impact of tumor size on patient survival, tumor recurrence and TNM staging," J Urol Dec. 1999;162(6):1930-3.
Hall et al., in vivo real-time freehand palpation imaging Ultrasound Med Biol. Mar. 2003; 29(3):427-35.
Hinshaw et al., "Multiple-Electrode Radiofrequency Ablation of Symptomatic Hepatic Cavernous Hemangioma," Am. J. Roentgenol., vol. 189, Issue 3, W-149, Sep. 1, 2007.
Hock et al., "Increasing incidence of all stages of kidney cancer in the last 2 decades in the United States: an analysis of surveillance, epidemiology and end results program data," J Urol 2002; 167:57-60. Ovid Full Text Bibliographic Links.
Hollenbeck et al., "National utilization trends of partial nephrectomy for renal cell carcinoma: a case of underutilization?" Urology Feb. 2006;67(2):254-9.
Huang et al., "Partial nephrectomy versus radical nephrectomy in patients with small renal tumors—is there a difference in mortality and cardiovascular outcomes?" J Uro Jan. 2009;181(1):55-61; discussion-2.
Ismail et al., "3D-guided CT reconstruction using time-of-flight camera," Accepted in SPIE Medical Imaging 2011.
Jemal et al., "Cancer statistics," 2008. CA Cancer J Clin 2008; 58:71-96. SFX.
Jemal et al., "Cancer statistics," 2007. CA Cancer J Clin Jan.-Feb. 2007;57(1):43-66.
Koichi et al., "Insufficient radiofrequency ablation therapy may induce further malignant transformation of hepatocellular carcinoma," Journal of Hepatology International, vol. 2, No. 1, Mar. 2008, pp. 116-123.
Koniaris et al., "Focal hepatic ablation using interstitial photon radiation energy," J Am Coll Surg. Aug. 2000;191(2):164-74.
Konofagou, "Quo vadis elasticity imaging?" Ultrasonics. Apr. 2004; 42(1-9):331-6.
Kunkle et al., "Excise, ablate or observe: the small renal mass dilemma—a meta-analysis and review," J Urol Apr. 2008; 179(4):1227-33; discussion 33-4.
Leibovich et al., "Nephron sparing surgery for appropriately selected renal cell carcinoma between 4 and 7 cm results in outcome similar to radical nephrectomy," J Urol Mar. 2004;171(3):1066-70.
Lyshchik et al., "Thyroid gland tumor diagnosis at US elastography," Radiology. Oct. 2005;237(1):202-11.
Moinzadeh et al., "Laparoscopic partial nephrectomy: 3-year followup," J Urol Feb. 2006;175(2):459-62.
Mulier et al., "Local recurrence after hepatic radiofrequency coagulation: multivariate meta-analysis and review of contributing factors," Ann Surg. Aug. 2005;242(2):158-71.
Ophir et al., "Elastography: a quantitative method for imaging the elasticity of biological tissues," Ultrasonic Imag., 13:111-134, 1991.
Partridge et al., "Accuracy of MR imaging for revealing residual breast cancer in patients who have undergone neoadjuvant chemotherapy," AJR Am J Roentgenol. Nov. 2002; 179(5):1193-9.
Poon et al., "Learning curve for radiofrequency ablation of liver tumors: prospective analysis of initial 100 patients in a tertiary institution," Ann Surg. Apr. 2004; 239(4):441-9.
Purohit et al., "Imaging clinically localized prostate cancer," Urol Clin North Am. May 2003;30(2):279-93.
Rivaz et al., "Ablation monitoring with elastography: 2D in-vivo and 3D ex-vivo studies," International Conference on Medical Image Computing and Computer-Assisted Intervention, MICCAI 2008.
Rivaz et al., "Tracked Regularized Ultrasound Elastography for Targeting Breast Radiotherapy," Medical Image Computing and Computer Assisted Intervention (MICCAI) 2009.
Rosen et al., "Accuracy of MRI in the detection of residual breast cancer after neoadjuvant chemotherapy," AJR Am J Roentgenol. Nov. 2003; 181(5):1275-82.
Scott et al., "Accuracy and effectiveness of laparoscopic vs open hepatic radiofrequency ablation," Surg Endosc. Feb. 2001;15(2):135-40.
Smith et al., "Positron emission tomography using [(18)F]-fluorodeoxy-D-glucose to predict the pathologic response of breast cancer to primary chemotherapy," J Clin Oncol. Apr. 2000;18(8):1676-88.
Stolka et al., "A 3D-elastography-guided system for laparoscopic partial nephrectomies". SPIE Medical Imaging 2010 (San Diego, CA/USA) 76251-12.
Thompson et al., "Radical nephrectomy for pT1a renal masses may be associated with decreased overall survival compared with partial nephrectomy," J Urol2008 Feb; 179(2):46871; discussion 72-3.
Valero et al., "Locally Advanced Breast Cancer," Oncologist. 1996; 1(1 & 2):8-17.
van Duijnhoven et al., "Factors influencing the local failure rate of radiofrequency ablation of colorectal liver metastases," Ann Surg Oncol. May 2006; 13(5):651-8. Epub Mar. 17, 2006.
Varghese et al., Elastographic imaging of thermal lesions in liver in-vivo using diaphragmatic stimuli. Ultrason Imaging. Jan. 2004;26(1):18-28.
Volpe et al., "The natural history of incidentally detected small renal masses," Cancer Feb. 15, 2004;100(4):738-45.
Volpe et al., "The natural history of small renal masses," Nat Clin Pract Urol 2005; 2:384-390.
Wood et al., "Radiofrequency ablation of 231 unresectable hepatic tumors: indications, limitations, and complications," Ann Surg Oncol. Sep. 2000;7(8):593-600.
Xu et al., "Statistical Projection Completion in X-ray CT Using Consistency Conditions," Medical Imaging, IEEE Transactions on , vol. 29, No. 8, pp. 1528-1540, Aug. 2010.
Zini et al., "Radical versus partial nephrectomy: effect on overall and noncancer mortality," Cancer Apr. 1, 2009;115(7):1465-71.
Stolka et al. "Navigation with local sensors in handheld 3D ultrasound: initial in-vivo experience," SPIE Medical Imaging 2011, Lake Buena Vista, FL/USA, pp. 79681J-79681J, International Society for Optics and Photonics, 2011.
Wang et al. "The Kinect as an interventional tracking system," SPIE Medical Imaging, San Diego, CA, USA, pp. 83160U-83160U, International Society for Optics and Photonics, 2012.
E.M. Petriu "Absolute Position Measurement Using Pseudo-Random Binary Encoding" School of Information Technology and Engineering, University of Ottawa, available at http://www.csi.uottawa.ca/~petriu/ELG5161-PRBS-encoding.pdf.
Image Guided Surgical Interventions, Current Problems in Surgery, vol. 46, pp. 730-766, Sep. 2009, available at <http://biorobotics.harvard.edupubs/2009/CurrentProblemsInSurgery.pdf>.
Baumhauer et al., Navigation in Endoscopic Soft Tissue Surgery: Perspectives and Limitations, Journal of Endourology, Apr. 2008, 22(4): 750-766, available at http://online.liebertpub.com/doi/abs/10.1089/end.2007.9027.
International Search Report and Written Opinion issued in PCT Application No. PCT/US2014/067441 dated Mar. 17, 2015.

\* cited by examiner

US 9,668,819 B2

SURGICAL NEEDLE FOR A SURGICAL SYSTEM WITH OPTICAL RECOGNITION

RELATED APPLICATION

This patent application is a continuation of U.S. patent application Ser. No. 14/092,843, filed Nov. 27, 2013. U.S. patent application Ser. No. 14/092,843 is hereby incorporated by reference in its entirety.

FIELD OF INVENTION

The field of the currently claimed embodiments of this invention relate to surgical needles for use with imaging devices, and more particularly to imaging devices with one or more sensors for observation and tracking of one or more surgical needles.

DISCUSSION OF RELATED ART

In image-guided interventions, the tracking and localization of imaging devices and medical tools during procedures are exceptionally important and are considered the main enabling technology in image-guided surgery (IGS) systems. Tracking technologies may be categorized into the following groups: 1) mechanical-based tracking including active robots (e.g., DaVinci robot) and passive-encoded mechanical arms (e.g., Faro mechanical arms), 2) optical-based tracking, 3) acoustic-based tracking, and 4) electromagnetic (EM)-based tracking.

Ultrasound is one useful imaging modality for image-guided interventions including ablative procedures, biopsy, radiation therapy, and surgery. In the literature and in research labs, ultrasound-guided intervention research is performed by integrating a tracking system (either optical or EM methods) with an ultrasound (US) imaging system to, for example, track and guide liver ablations, or in external beam radiation therapy [E. M. Boctor, M. DeOliviera, M. Choti, R. Ghanem, R. H. Taylor, G. Hager, G. Fichtinger, "Ultrasound Monitoring of Tissue Ablation via Deformation Model and Shape Priors", International Conference on Medical Image Computing and Computer-Assisted Intervention, MICCAI 2006; H. Rivaz, I. Fleming, L. Assumpcao, G. Fichtinger, U. Hamper, M. Choti, G. Hager, and E. Boctor, "Ablation monitoring with elastography: 2D in-vivo and 3D ex-vivo studies," International Conference on Medical Image Computing and Computer-Assisted Intervention, MICCAI 2008; H. Rivaz, P. Foroughi, I. Fleming, R. Zellars, E. Boctor, and G. Hager, "Tracked Regularized Ultrasound Elastography for Targeting Breast Radiotherapy", Medical Image Computing and Computer Assisted Intervention (MICCAI) 2009]. Current commercial systems may include integrating an EM tracking device into high-end cart-based US system. Small EM sensors may be integrated into the ultrasound probe, and similar sensors may be attached and fixed to the intervention tool of interest.

Limitations of the current approach on both the research and commercial sides may be attributed to the available tracking technologies and to the feasibility of integrating these systems and using them in clinical environments. For example, mechanical-based trackers are considered expensive and intrusive solutions, i.e. they require large space and limit user motion. On the other hand, acoustic tracking does not provide sufficient navigation accuracy. Optical and EM tracking technologies require intrusive setups with a base camera (in case of optical tracking methods) or a reference EM transmitter (in case of EM methods). Additionally, optical rigid-body or EM sensors have to be attached to the imager and all needed tools, hence offline calibration and sterilization steps are required. Thus, there remains a need for improved imaging devices for use in image-guided surgery.

SUMMARY

Aspects of the invention may involve systems, tools, and methods. In one embodiment, a system for image-guided surgery may be provided. The system may include a visual imaging system; a medical tool comprising a shaft and a tip, wherein the shaft of the tool includes an optically detectable feature that allows a position of the tip to be determined; and a display configured to display a real-time representation of the medical tool including the position of the tip regardless of whether the tip is obstructed or visible.

In another embodiment, a tool for use with an image-guided surgical system may be presented. The tool may include a tip; and a shaft at least one of integral with or attached to the tip, wherein the shaft includes a pattern at least one of marked, printed, etched, or applied to the shaft of the tool, and wherein the pattern is suitable to be used by an image-guided surgical system to determine positions of said tip in real-time irrespective of whether said tip is obscured in corresponding images.

In yet another embodiment, a method for image guided surgery may be presented. The method may include receiving, by one or more processors, input from one or more light-sensitive devices, the input including light reflected from a shaft of a tool, wherein the shaft of the tool includes one or more visible features; calculating, by the one or more processors, one or more candidate tip locations in a three dimensional space using the one or more visible features; and displaying, by the one or more processors, an insertion depth of the tip and the one or more candidate tip locations.

BRIEF DESCRIPTION OF THE DRAWINGS

Further objectives and advantages will become apparent from a consideration of the description, drawings, and examples.

DETAILED DESCRIPTION

Figure 1:
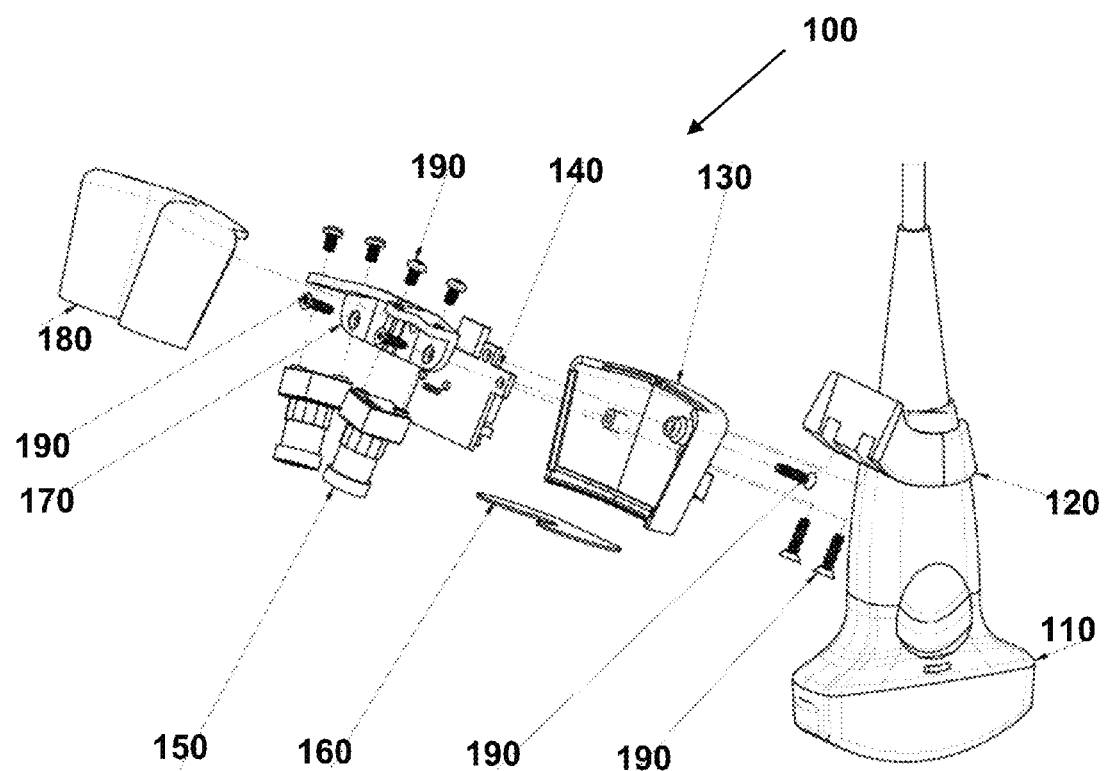
FIG. 1 shows an embodiment of an imaging component for an imaging system according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Use of the term needle and/or medical tool may refer to an elongated medical tool such as a needle, a pointer, a biopsy tool, a laparoscope, an ablation device, a surgical instrument, and/or an elongated tool.

Some embodiments of this invention describes IGI-(image-guided interventions)-enabling "platform technology" going beyond the current paradigm of relatively narrow image-guidance and tracking. It simultaneously aims to overcome limitations of tracking, visualization, and guidance; specifically using and integrating techniques e.g. related to medical tool identification and tracking using 3D computer vision and structured light; and imaging device tracking using local sensing approaches; among others. Examples of IGI may be seen in U.S. patent application Ser. No. 13/511,101, titled "Low-cost image-guided navigation and intervention systems using cooperative sets of local sensors," published as U.S. Patent Application Publication No. 2013/0016185.

The current invention covers a wide range of different embodiments, sharing a tightly integrated common core of components and methods used for general imaging, projection, vision, and local sensing.

Some embodiments of the current invention are directed to combining a group of complementary technologies to provide a local sensing approach that can provide enabling technology for the tracking of medical imaging devices, for example, with the potential to significantly reduce errors and increase positive patient outcomes. This approach can provide a platform technology for the tracking of ultrasound probes and other imaging devices, intervention guidance, and information visualization according to some embodiments of the current invention. By combining ultrasound imaging with image analysis algorithms and probe-mounted light-sensitive devices, independent optical-inertial sensors, according to some embodiments of the current invention, it is possible to reconstruct the position and trajectory of surgical medical tools and other tools or objects by incrementally tracking their current motion.

Some embodiments of the current invention allow the segmentation, tracking, and guidance of medical tools and other tools (using visual, ultrasound, and/or other imaging and localization modalities).

Such devices can allow imaging procedures with improved sensitivity and specificity as compared to the current state of the art. This can open up several possible application scenarios that previously required harmful X-ray/CT or expensive MRI imaging, and/or external tracking, and/or expensive, imprecise, time-consuming, or impractical hardware setups, or that were simply afflicted with an inherent lack of precision and guarantee of success, such as: biopsies, RF/HIFU ablations etc.: can allow 2D- or 3D-ultrasound-based medical tool guidance, brachytherapy: can allow 3D-ultrasound acquisition and medical tool guidance for precise brachytherapy seed placement, other applications relying on tracked imaging and tracked tools.

Some embodiments of the current invention may provide several advantages over existing technologies, such as combinations of: low-cost tracking, local, compact, and non-intrusive solution—ideal tracking system for hand-held and compact ultrasound systems that are primarily used in intervention and point-of-care clinical suites, but also for general tool tracking under visual tracking in other interventional settings.

For example, some embodiments of the current invention are directed to devices and methods for the tracking of ultrasound probes and other imaging devices. By combining ultrasound imaging with image analysis algorithms and probe-mounted light-sensitive devices it is possible to reconstruct the position and trajectory of surgical tools and other objects by incrementally tracking their current motion according to an embodiment of the current invention. This can provide several possible application scenarios that previously required expensive, imprecise, or impractical hardware setups. For example, 3D ultrasound-based medical tool guidance.

Current sonographic procedures mostly use handheld 2D ultrasound (US) probes that return planar image slices through the scanned 3D volume (the "region of interest" (ROI)). For percutaneous interventions requiring medical tool guidance, prediction of the medical tool trajectory is currently based on tracking with sensors attached to the distal (external) medical tool end and on mental extrapolation of the trajectory, relying on the operator's experience. An integrated system with 3D ultrasound, medical tool tracking, medical tool trajectory prediction and interactive user guidance would be highly beneficial.

FIG. 1 shows an embodiment of an imaging component 100 for an imaging system according to an embodiment of the current invention. Imaging component 100 includes an imaging tool 110, bracket 120 that is structured to be attachable to imaging tool 110. In the example of FIG. 1, the imaging tool 110 is an ultrasound probe and bracket 120 is structured to be attached to a probe handle of the ultrasound probe. Ultrasound probes may include, for example, Ultrasonix #C5-2. However, the broad concepts of the current invention are not limited to only this example. The bracket 120 can be structured to be attachable to other handheld instruments for image-guided surgery, such as surgical orthopedic power tools or stand-alone handheld brackets, for example. In other embodiments, the bracket 120 can be structured to be attachable to the C-arm of an X-ray system or an MRI system, for example.

Imaging component 100 may include top shell 180 and bottom shell 130 that may be coupled together to form a head shell. Top shell 180 and bottom shell 130 may be coupled securely to stabilization assembly 170 (e.g., a stabilization bar). Head shell may house stabilization assembly 170 other components of imaging component 100. Screws 190 may be used to couple together the components of imaging component 100.

Imaging component 100 may also include one or more light-sensitive devices 150 (or light sensitive devices) securely attached to stabilization assembly 170. The one or more light-sensitive devices 150 may be at least one of a visible-light camera, an infra-red camera, a time-of-flight camera, PSDs (position-sensitive devices), and/or reflection-based laser sensing in some embodiments of the current invention. The one or more light-sensitive devices 150 may be arranged to observe a surface region close to the and during operation of the imaging component 100. In the embodiment of FIG. 1, the one or more light-sensitive devices 150 may be arranged and configured for stereo observation of a region of interest.

Imaging component 100 may also include a printed circuit board 140 that may include one or more microprocessors, one or more light-emitting devices, and a memory device. The light-emitting device may emit light in the visible spectrum, infrared, ultraviolet, or other spectrum. The light-emitting device may include at least one of LEDs, light bulbs, CFLs, lasers, etc. The printed circuit board may also be connected to one or more light-sensitive devices 150 and may be securely coupled to stabilization assembly 170.

Imaging component 100 may also include lens 160 that provides a screen for one or more light-sensitive devices 150. In one embodiment, lens 160 may be made of ultra-tough gorilla glass of 0.031" thickness. Lens 160 may be frosted and/or partially frosted to diffuse the light emitted from the one or more light-emitting devices. Light from the light-emitting devices may be diffused through a plane of frosted glass, mesh, translucent tape, or other means.

Figure 2:
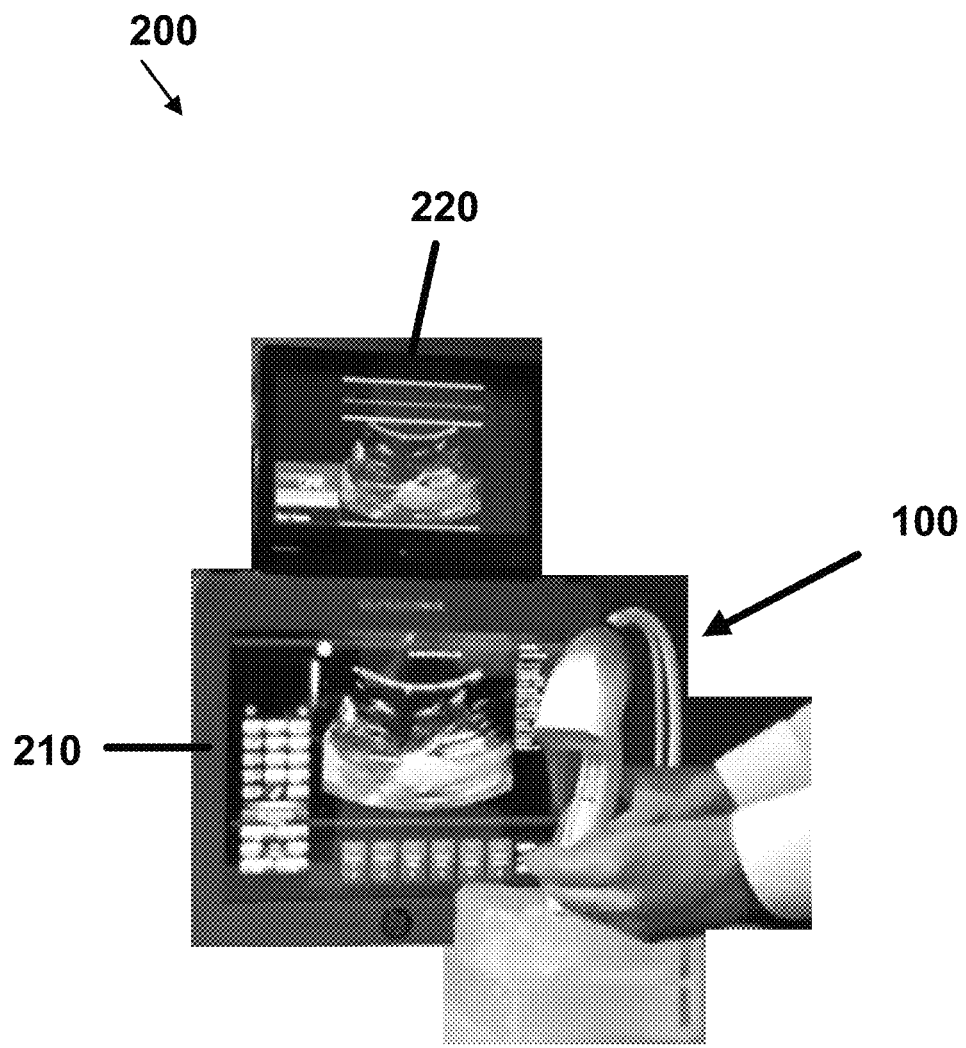
FIG. 2 shows an embodiment of an imaging system according to an embodiment of the current invention.

FIG. 2 shows an embodiment of imaging system 200 according to an embodiment of the current invention. Imaging system 200 includes imaging component 100 being controlled by a user. The user is also inserting a medical tool. Imaging system 200 includes image display 210. Image display may 210 display output from imaging tool 110 such as sonogram images. Imaging system 200 also includes augmented display 220. Augmented display 220 may be a touch screen and allow input from the user. Augmented display 220 may overlay tracking information on top of output from imaging tool 110. Tracking information may include current tracking status, current location, and current insertion depth of the medical tool, surgical instrument, or other tool being inserted by the user. Overlaid information may also include medical tool tip location and medical tool tip distance to a selected target.

Although FIGS. 1 and 2 illustrate the imaging system as an ultrasound imaging system and that the bracket 120 is structured to be attached to an imaging tool 110 as an ultrasound probe, the broad concepts of the current invention are not limited to this example. The bracket may be structured to be attachable to other imaging systems, such as, but not limited to, x-ray and magnetic resonance imaging systems, for example.

Figure 3:
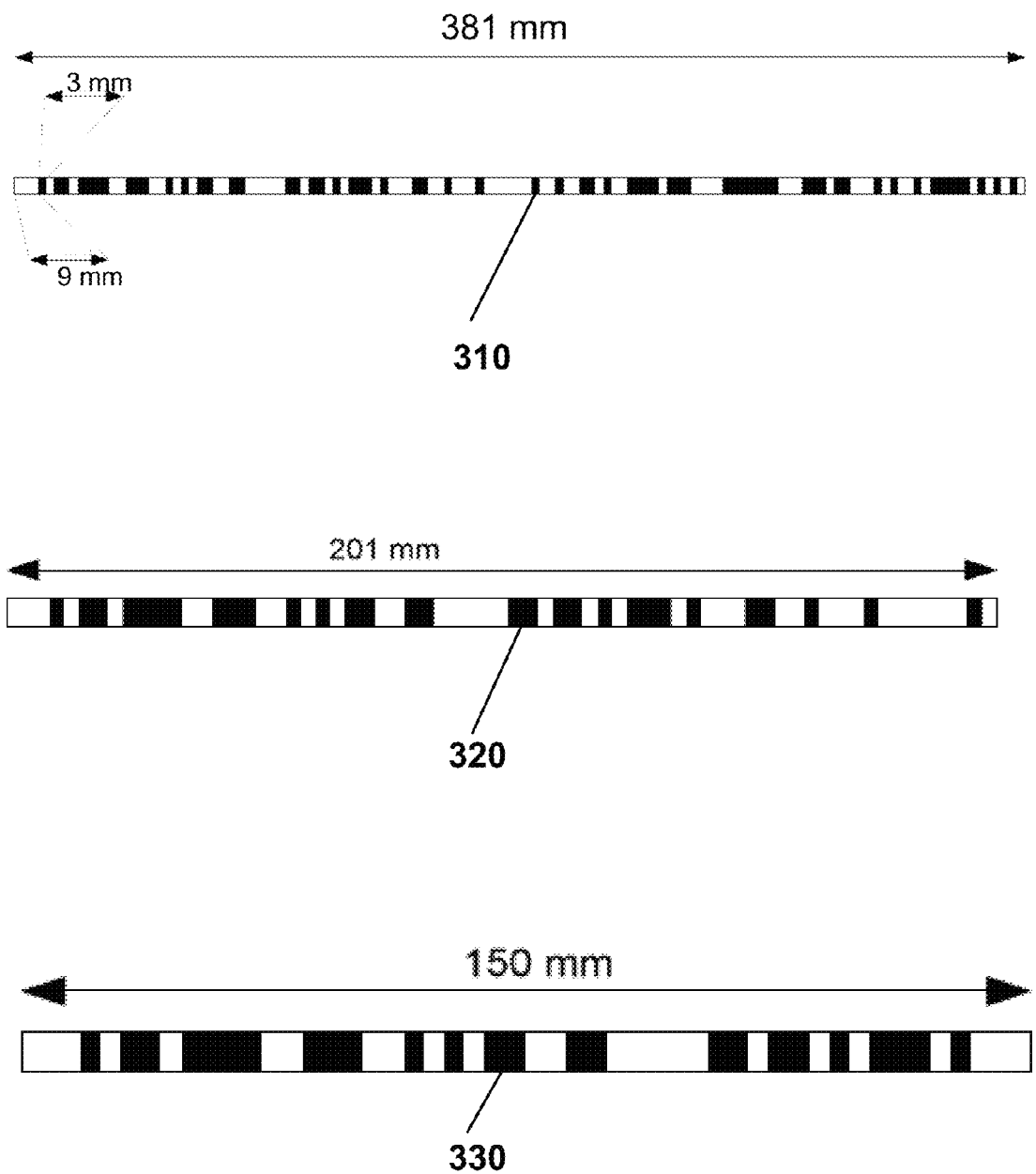
FIG. 3 depicts a sample tracking pattern according to an embodiment of the current invention.

FIG. 3 depicts a sample tracking patterns according to an embodiment of the current invention. Medical tools 310, 320, 330 are 381 mm, 201 mm, and 150 mm long, respectively, and depict a tracking pattern of the same length. The medical tool may include a shaft and a tip. The tracking patterns may be marked, printed, etched, or otherwise applied onto the medical tool shaft or other linear tool. Imaging system 200 may resolve the pattern on the shaft of a medical tool or other linear tool. The tracking patterns may include a sequence in which each subsequence of a given minimal length appears only once. The tracking patterns may include a pseudo random binary sequence (PRBS), a De Bruijn sequence, or barcodes. The pattern may be a sequence generated as described in "Absolute Position Measurement Using Pseudo-Random Binary Encoding" By E. M. Petriu, and herein incorporated by reference.

Additionally, tracking patterns may include rings on a medical tool, proprietary pseudo-random binary sequence (PRBS) patterns or a De Bruijn sequence applied onto the medical tool shaft. Imaging system 200 may track the medical tool insertion depth visually, using the discernible part of the pattern to identify the medical tool and determine the section and thus the position of the medical tool tip, either uniquely or up to a finite set of discrete possibilities. The determined depth may be overlaid on medical tool guidance displays (e.g., augmented display 220) with one or multiple medical tool-tip candidate locations. The medical tool guidance display may be configured to display a real-time representation of the medical tool including the position of the tip of the medical tool regardless of whether the tip is obstructed or visible. Due to the nature of the pattern, the visual imaging system may correctly calculates the insertion depth when a portion of the pattern is not viewable by the visual imaging system or when only a portion of a minimum length of the pattern is viewable by an imaging system. Indeed, the visual imaging system may correctly calculates a insertion depth when at least a fraction ($n/k''$) of the complete pattern is viewable, if each distinct element of the pattern can have k different values (such as colors or shades) and the complete pattern is $k''$ elements long.

The tracking pattern may be initially algorithmically generated as follows: Pseudo random binary code of length $2^n-1$ is generated as described in "Absolute Position Measurement Using Pseudo-Random Binary Encoding" By E. M. Petriu located at http://www.csi.uottawa.ca/~petriu/ELG5161-PRBS-encoding.pdf. In this technique, the sequence is started with an arbitrary sequence of n binary values (bits). Exclusive-OR of two bits in specific positions is then computed and added to the end of the sequence resulting in n+1 bits. This procedure is repeated for the last n bits in the sequence until $2^n-1$ bits are generated. The tracking pattern may be non-periodic and may provide a unique position on the medical tool. The pattern may provide that no matter which part of the medical tool is visible, imaging system 200 may localize on the medical tool with the pattern and detect insertion depth. All medical tools may have the same pattern, but may also have distinct patterns to help disambiguating tools within the visible area.

In another embodiment, an attachment such as a clip-on ring may sit securely on the medical tool. The medical tool with the ring may be demonstrated to imaging system 200, which determines the distance from attachment or ring to medical tool tip, and uses that distance for tip position estimation. The ring may be circular, oval, cylindrical, or handle shaped. The attachment or clip-on may also be reflective (e.g., IR-reflective).

The pattern on the medical tool may be IR reflective pattern. The IR reflectiveness may aid in the detection of the medical tool and assist in eliminating false positives. Imaging system 200 may include a light sensitive device with a filter that lets pass light of a specific wavelength and an illumination source which illuminates the medical tool and a coating on the medical tool which, in response to the illumination, produces or reflects light at the wavelength of the filter of the light sensitive device. The light sensitive device may include one or more light-sensitive devices 150 or one or more PSDs or some combination thereof. Furthermore, the medical tool may have both visible and IR-visible patterns or rings applied to it. This would allow the operator to use medical tools that seem generic (e.g., that carry centimeter-markings), but indeed carry information invisible to the human eye (but visible to the light-sensitive devices) and useful for localization.

In other embodiments, the pattern may be used for rejection or minimization of false-positive-detections of medical tools. In other words, by only detecting objects that carry the expected visible features the system may avoid detecting and/or tracking non-important objects. The pattern may also be used for disambiguation of tools, different models of which are differentiated by distinct combinations of visible features, for example. The pattern may also be used to decide on the suitability of a tool for a desired or current use (e.g., to reach a target at a certain depth). If the tool is not suitable, warnings may be displayed to the operator if an inappropriate tool is being used. The pattern may be used to verify the calibration between light-sensitive devices or light-sensitive devices that observe the feature-carrying tool. Such verification may be achieved by comparing the apparent (e.g., measured) height of the features in the data sets from the two or more light-sensitive devices, and by rejecting calibration if said heights differ. The patterns may also be used to improve tool detection, by only processing observed objects that exhibit a required pattern.

Figure 4:
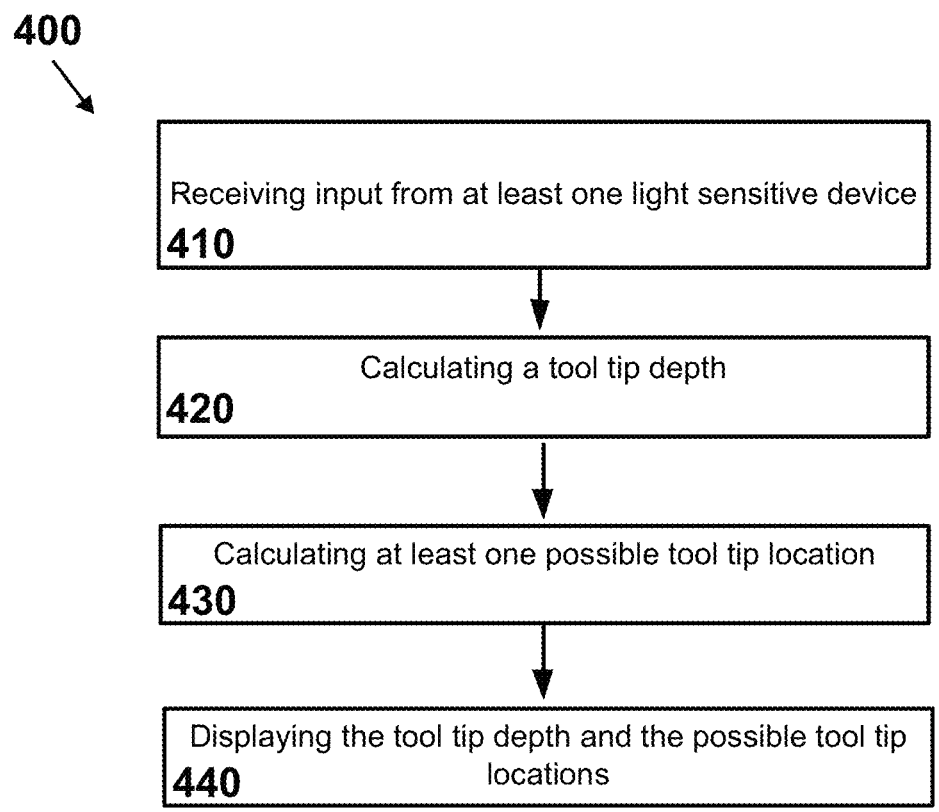
FIG. 4 depicts an example workflow according to an embodiment of the current invention.

FIG. 4 depicts example workflow 400 according to an embodiment of the current invention. In step 410, at least one light sensitive device 150 may receive light. The received light may include light reflected from a shaft of a medical tool. The shaft or other tool may include one or more visible features. The one or more visible features may include a detectable pattern, the pattern being initially created using a pseudo random binary code, wherein the pattern is one of marked, printed, etched, or applied to the shaft of the medical tool.

In another embodiment, the visible feature may include a ring attached to the medical tool shaft. The ring may be reflective and/or cylindrical or handle shaped. The ring may include a detectable pattern used in calculating an insertion depth of the tip of the medical tool, the detectable pattern may be initially created using a pseudo random binary code. Imaging system 200 may initially calculate a distance from the ring to the tip of the medical tool and use this calculated distance to calibrate the imaging system 200 for medical tool tracking From 410, flow may move to 420.

In 420, an insertion depth of the tip of the medical tool may be calculated. The depth calculation may be made based on the one or more visible features on the medical tool shaft. Because of the nature of the visible feature, the insertion depth of the tip of the medical tool may be correctly calculated even when a portion of the one or more visible features is not viewable by the one or more light sensitive devices. For example, when the visible feature includes the detectable pattern created using a pseudo random binary code, the pattern is non-periodic and, therefore, even if a small portion of the pattern is visible, imaging system 200 may still calculate the insertion depth. From 420, flow may move to 430.

In 430, at least one medical tool tip location may be calculated (e.g., candidate tip locations) using the one or more visible features. The calculated tip locations may be in a three dimensional plane and may be based on the insertion location, calculated insertion depth, and angle of entry of the medical tool. From 430, flow may move to 440.

In 440, the insertion depth of the tip of the medical tool and the possible tip locations may be displayed on augmented display 220. A surgeon or other medical personal may use the displayed information when performing an IGI, for example. From 440, flow may end.

In an embodiment, tracking of the medical tool may be accomplished through one or more visible features on the tool. (Basic tool tracking has been described in previous publications by the inventors, such as Stolka et al. "Navigation with local sensors in handheld 3D ultrasound: initial in-vivo experience," SPIE Medical Imaging 2011, Lake Buena Vista, Fla./USA, pp. 79681J-79681J. International Society for Optics and Photonics, 2011, and Wang et al. "The Kinect as an interventional tracking system," SPIE Medical Imaging, San Diego, Calif., USA, pp. 83160U-83160U. International Society for Optics and Photonics, 2012, both of which are included by reference in their entirety.) The visible feature may include a detectable pattern, the pattern being initially created using a pseudo random binary sequence, or more generally a de Bruijn sequence, wherein the pattern is one of marked, printed, etched, or applied to the tool. The pattern may be used to detect insertion depth of the tool into a human or animal body. Alternatively, the visible feature may include an attachment such as a ring attached to the tool. The ring may be reflective and/or cylindrical or handle shaped. The ring may include a detectable pattern used in calculating an insertion depth of the tip of the tool, the detectable pattern may be initially created using a pseudo random binary sequence. Imaging system 200 may initially calculate a distance from the ring to the tip of the tool and use this calculated distance to calibrate the imaging system 200 for tool tracking.

The displayed information to assist in medical tool positioning may include information about the length of intersection between the medical tool and the non-infinitesimally thin ultrasound imaging plane, by drawing markers on the medical tool line to denote the extent of said intersection. In other words, a line may indicate the medical tool trajectory, wherein a portion of the line may be shaded differently to indicate the area where the medical tool will cross the imaging plane of the ultrasound Insertion depth calculation may be made based on the one or more visible features on the tool. Because of the nature of the visible feature, the insertion depth of the tip of the tool may be correctly calculated even when a portion of the one or more visible features is not viewable by the one or more light sensitive devices. For example, when the visible feature includes the detectable pattern created using a pseudo random binary sequence, the pattern is non-periodic and unique over small segments. Therefore, even if a small portion of the pattern is visible, imaging system 200 may still calculate the insertion depth. Tool tip location may be calculated (e.g., candidate tip locations) using the one or more visible features. The calculated tip locations may be in three dimensional space and may be based on the insertion location, calculated insertion depth, and angle of entry of the medical tool. Insertion depth of the tool tip and possible tip locations may be displayed on augmented display 220. A surgeon or other medical personal may use the displayed information when performing an IGI, for example.

The following describes one possible technique of localizing the medical tool tip in stereo images using the pattern on the medical tool shaft in an embodiment. Given a pair of stereo images (left and right light-sensitive device images) and light-sensitive device calibration (intrinsic and extrinsic light-sensitive device parameters), the first step of tip localization is to rectify the left and right images. Next, the medical tool is detected in these images as straight lines centered at the middle of the shaft. In order to localize the tip of the medical tool in 3D, the medical tool line is reconstructed in 3D space. This line is then sampled with a constant delta providing a set of 3D points. These points are then projected back into the left and right images resulting in two sets of 2D points for the left and right rectified images. Then, the pixel intensities at these points are computed using interpolation. This will generate two intensity vectors with regular sampling. In the next step, the two intensity vectors are correlated against all possible "sub-patterns". A sub-pattern is a minimal continuous portion of the whole pattern that could be uniquely identified. For each sub-pattern, the location that maximizes correlation and the correlation value is recorded. The sub-patterns with the highest correlation value is selected in the left and right vectors. Since the offset of the sub-pattern with respect to the tip is known, the 3D location of the tip can be estimated. Note that left and right images provide two almost independent estimates of the tip location. As a verification step, the two estimated tip locations should be closer than a threshold. The final tip location is given as the weighted-average of these two estimated tip positions.

Figure 6:
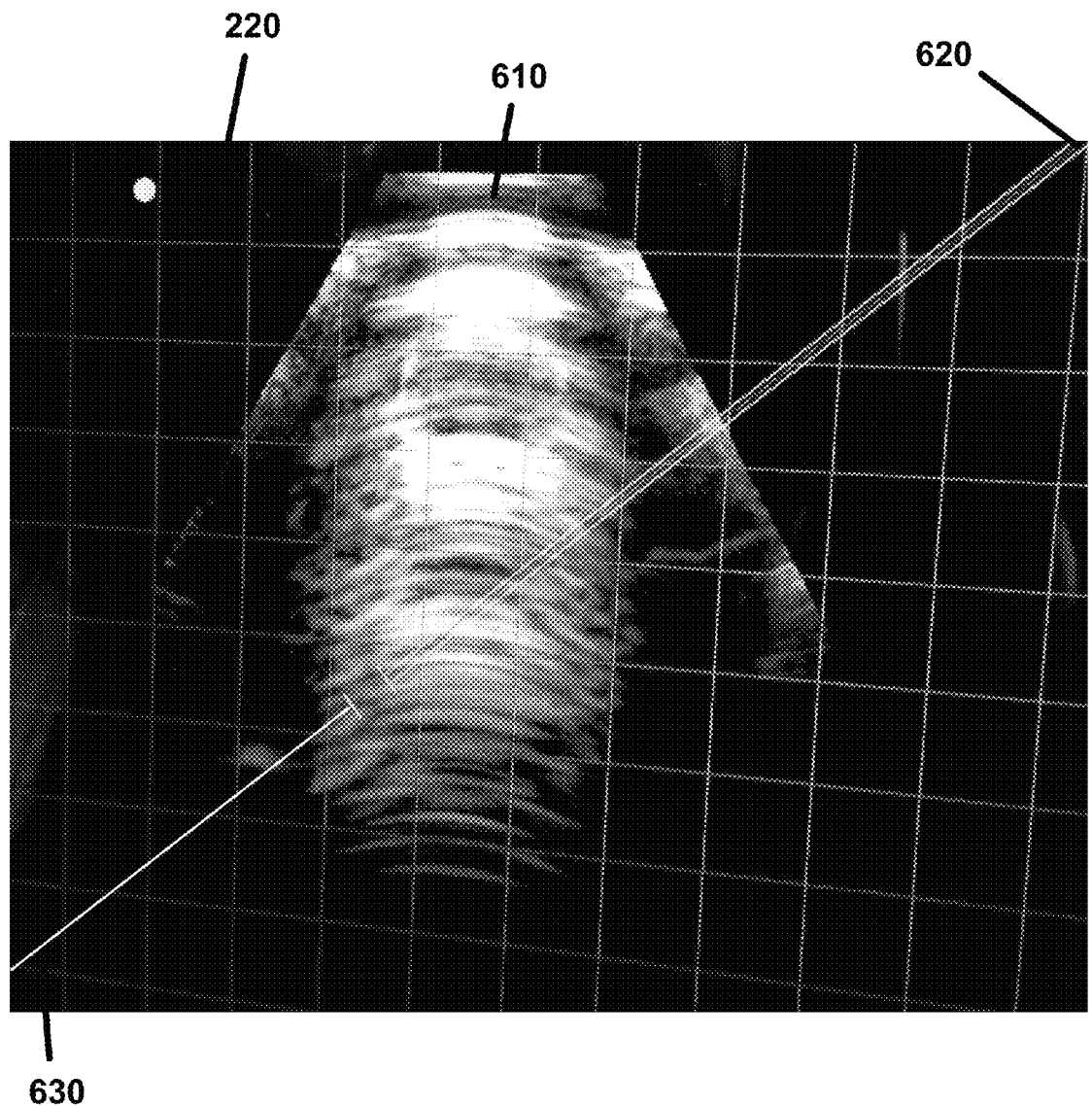
FIG. 6 shows a screenshot of a tool-tip display in an embodiment.

FIG. 6 shows a screenshot of a tool-tip display in an embodiment. FIG. 6 includes a screen shot from display 220 including ultrasound images 610. Display 220 also shows a representation of the medical tool 620 indicating the tool's current position (indicated by a double green line) including the tip (indicated by perpendicular lines) and a line indicating the future trajectory 630.

In another embodiment, light waves may be filtered by the one or more light sensitive devices to only allow light of a specific wavelength and to restrict light of other wavelengths. A coating may be applied to the medical tool that may be illuminated based on receiving light of a specific wavelength. The coating may produce or reflect a light of the specific wavelength. The reflected or produced light of a specific wavelength may be detected by the light sensitive devices. The reflected or produced light of a specific wavelength may reduce the occurrence of false positives. Further, the coating may only illuminate or produce light of a specific wavelength to reveal the detectable pattern. The possible tip locations and insertion depth of the tip of the medical tool may be calculated based on based on the displayed detectable pattern of light in a specific wavelength.

Illustrative Computer System

Figure 5:
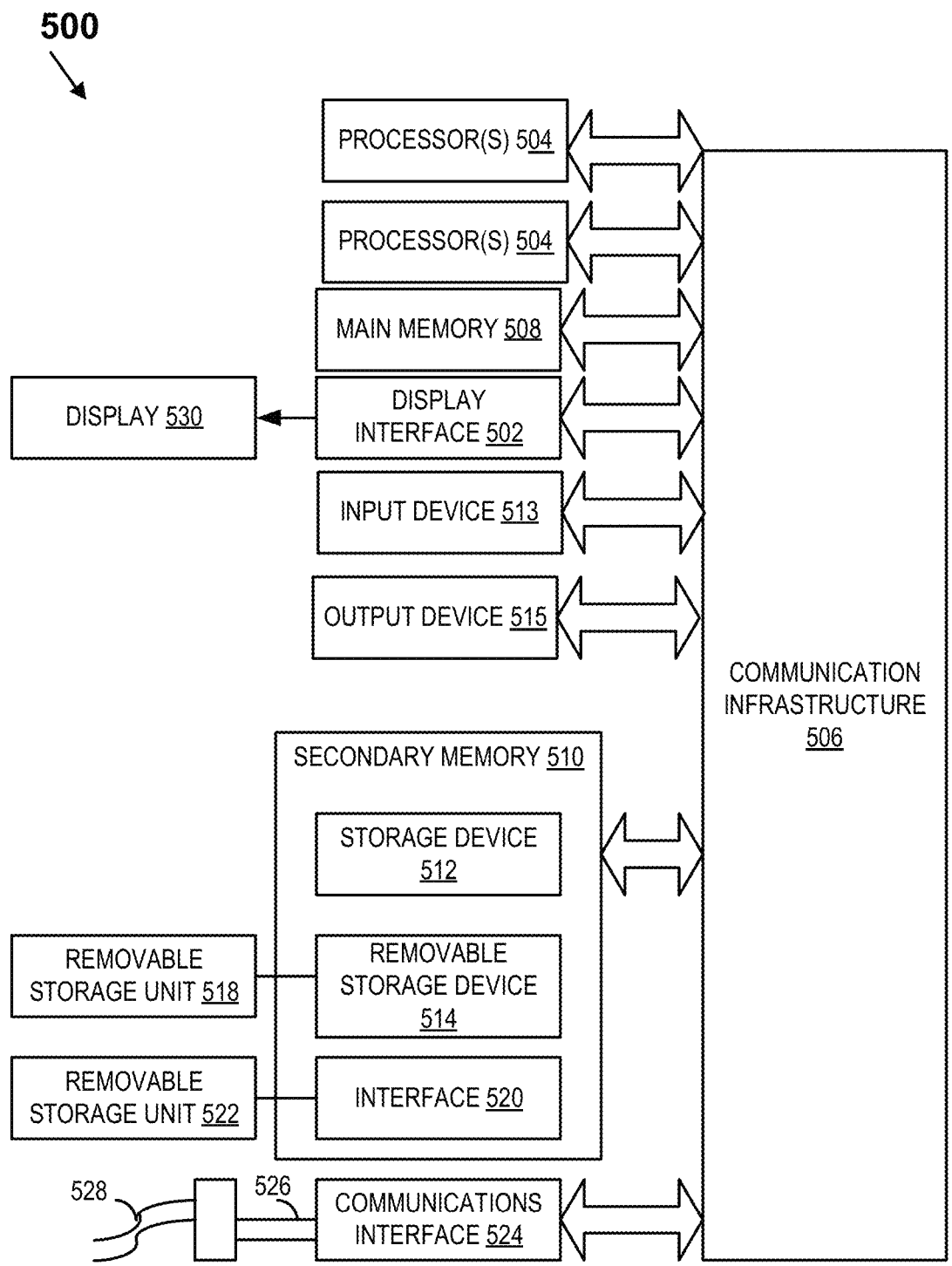
FIG. 5 depicts an illustrative embodiment of a computer for performing the methods and building the systems described herein.

FIG. 5 depicts an illustrative computer system that may be used in implementing an illustrative embodiment of the present invention. Specifically, FIG. 5 depicts an illustrative embodiment of a computer system 500 that may be used in computing devices such as, e.g., but not limited to, stand-alone or client or server devices. FIG. 5 depicts an illustrative embodiment of a computer system that may be used as client device, or a server device, etc. The present invention (or any part(s) or function(s) thereof) may be implemented using hardware, software, firmware, or a combination thereof and may be implemented in one or more computer systems or other processing systems. In fact, in one illustrative embodiment, the invention may be directed toward one or more computer systems capable of carrying out the functionality described herein. An example of a computer system 500 is shown in FIG. 5, depicting an illustrative embodiment of a block diagram of an illustrative computer system useful for implementing the present invention. Specifically, FIG. 5 illustrates an example computer 500, which in an illustrative embodiment may be, e.g., (but not limited to) a personal computer (PC) system running an operating system such as, e.g., (but not limited to) MICROSOFT® WINDOWS® NT/98/2000/XP/Vista/Windows 7/Windows 8/Surface, etc. available from MICROSOFT® Corporation of Redmond, Wash., U.S.A. or an Apple computer or tablet executing MAC® OS, OS X, or iOS from Apple® of Cupertino, Calif., U.S.A., or a computer running a Linux or other UNIX derivative. However, the invention is not limited to these platforms. Instead, the invention may be implemented on any appropriate computer system running any appropriate operating system. In one illustrative embodiment, the present invention may be implemented on a computer system operating as discussed herein. An illustrative computer system, computer 500 is shown in FIG. 5. Other components of the invention, such as, e.g., (but not limited to) a computing device, a communications device, a telephone, a personal digital assistant (PDA), an iPhone, a 3G/4G wireless device, a wireless device, a personal computer (PC), a handheld PC, a laptop computer, a smart phone, a mobile device, a netbook, a handheld device, a portable device, an interactive television device (iTV), a digital video recorder (DVR), client workstations, thin clients, thick clients, fat clients, proxy servers, network communication servers, remote access devices, client computers, server computers, peer-to-peer devices, routers, web servers, data, media, audio, video, telephony or streaming technology servers, etc., may also be implemented using a computer such as that shown in FIG. 5. In an illustrative embodiment, services may be provided on demand using, e.g., an interactive television device (iTV), a video on demand system (VOD), via a digital video recorder (DVR), and/or other on demand viewing system. Computer system 500 may be used to implement the network and components as described in FIGS. 1 and 2. Such as imaging component 100 and/or other devices of imaging system 200.

The computer system 500 may include one or more processors, such as, e.g., but not limited to, processor(s) 504. The processor(s) 504 may be connected to a communication infrastructure 506 (e.g., but not limited to, a communications bus, cross-over bar, interconnect, or network, etc.). Processor 504 may include any type of processor, microprocessor, or processing logic that may interpret and execute instructions (e.g., for example, a field programmable gate array (FPGA)). Processor 504 may comprise a single device (e.g., for example, a single core) and/or a group of devices (e.g., multi-core). The processor 504 may include logic configured to execute computer-executable instructions configured to implement one or more embodiments. The instructions may reside in main memory 508 or secondary memory 510. Processors 504 may also include multiple independent cores, such as a dual-core processor or a multi-core processor. Processors 504 may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Computer system 500 may include a display interface 502 that may forward, e.g., but not limited to, graphics, text, and other data, etc., from the communication infrastructure 506 (or from a frame buffer, etc., not shown) for display on the display unit 501. The display unit 501 may be, for example, a television, a computer monitor, or a mobile phone screen. The output may also be provided as sound through a speaker.

The computer system 500 may also include, e.g., but is not limited to, a main memory 508, random access memory (RAM), and a secondary memory 510, etc. Main memory 508, random access memory (RAM), and a secondary memory 510, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory 510 may include, for example, (but is not limited to) a hard disk drive 512 and/or a removable storage drive 514, representing a floppy diskette drive, a magnetic tape drive, an optical disk drive, a compact disk drive CD-ROM, flash memory, etc. The removable storage drive 514 may, e.g., but is not limited to, read from and/or write to a removable storage unit 518 in a well-known manner. Removable storage unit 518, also called a program storage device or a computer program product, may represent, e.g., but is not limited to, a floppy disk, magnetic tape, optical disk, compact disk, etc. which may be read from and written to removable storage drive 514. As will be appreciated, the removable storage unit 518 may include a computer usable storage medium having stored therein computer software and/or data.

In alternative illustrative embodiments, secondary memory 510 may include other similar devices for allowing computer programs or other instructions to be loaded into computer system 500. Such devices may include, for example, a removable storage unit 522 and an interface 520. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 522 and interfaces 520, which may allow software and data to be transferred from the removable storage unit 522 to computer system 500.

Computer 500 may also include an input device 503 which may include any mechanism or combination of mechanisms that may permit information to be input into computer system 500 from, e.g., a user. Input device 503 may include logic configured to receive information for computer system 500 from, e.g. a user. Examples of input device 503 may include, e.g., but not limited to, a mouse, pen-based pointing device, or other pointing device such as a digitizer, a touch sensitive display device, and/or a keyboard or other data entry device (none of which are labeled). Other input devices 503 may include, e.g., but not limited to, a biometric input device, a video source, an audio source, a microphone, a web cam, a video camera, light-sensitive device, and/or other camera.

Computer 500 may also include output devices 515 which may include any mechanism or combination of mechanisms that may output information from computer system 500. Output device 515 may include logic configured to output information from computer system 500. Embodiments of output device 515 may include, e.g., but not limited to, display 501, and display interface 502, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. Computer 500 may include input/output (I/O) devices such as, e.g., (but not limited to) input device 503, communications interface 524, cable 528 and communications path 526, etc. These devices may include, e.g., but are not limited to, a network interface card, and/or modems.

Communications interface 524 may allow software and data to be transferred between computer system 500 and external devices.

In this document, the terms "computer program medium" and "computer readable medium" may be used to generally refer to media such as, e.g., but not limited to, removable storage drive 514, a hard disk installed in hard disk drive 512, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to computer system 500. It should be noted that a computer-readable medium that comprises computer-executable instructions for execution in a processor may be configured to store various embodiments of the present invention. References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic.

Further, repeated use of the phrase "in one embodiment," or "in an illustrative embodiment," do not necessarily refer to the same embodiment, although they may. The various embodiments described herein may be combined and/or features of the embodiments may be combined to form new embodiments.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses for performing the operations herein. An apparatus may be specially constructed for the desired purposes, or it may comprise a general purpose device selectively activated or reconfigured by a program stored in the device.

Embodiments may be embodied in many different ways as a software component. For example, it may be a stand-alone software package, or it may be a software package incorporated as a "tool" in a larger software product, such as, for example, a scientific modeling product. It may be downloadable from a network, for example, a website, as a stand-alone product or as an add-in package for installation in an existing software application. It may also be available as a client-server software application, or as a web-enabled software application. It may also be part of a system for detecting network coverage and responsiveness. A general purpose computer may be specialized by storing programming logic that enables one or more processors to perform the techniques indicated herein and the steps of FIG. 4.

Embodiments of the present invention may include apparatuses for performing the operations herein. An apparatus may be specially constructed for the desired purposes, or it may comprise a general purpose device selectively activated or reconfigured by a program stored in the device.

Embodiments may be embodied in many different ways as a software component. For example, it may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application.

While various embodiments of the present invention have been described above, it should be understood that they have been presented by way of example only, and not limitation. Thus, the breadth and scope of the present invention should not be limited by any of the above-described illustrative embodiments, but should instead be defined only in accordance with the following claims and their equivalents.

We claim:

1. A system for image-guided surgery comprising:
an imaging probe;
a medical tool comprising a tip, wherein the medical tool includes an optically detectable non-repeating pattern extending along a sufficient portion of said tool such that at least a portion of said optically detectable non-repeating pattern remains visible outside of a patient during surgery so as to allow a position of the tip to be determined based on said visible portion;
a visual imaging system in communication with the imaging probe, the visual imaging system comprising a plurality of light-sensitive devices to be arranged outside of the patient, the light-sensitive devices being configured to generate an input and detect said portion of said optically detectable non-repeating pattern that is visible outside of said patient during surgery based on said input, the visual imaging system being configured to resolve the optically detectable non-repeating pattern to identify the medical tool and to track the medical tool; and
a display configured to display an image from the imaging probe and to overlay a real-time representation of the medical tool and tracking information over and registered to said image including the position of the tip, based on the resolved pattern, regardless of whether the tip is obstructed or visible.

2. The system of claim 1, wherein the medical tool comprises one of a needle, a pointer, a biopsy tool, a laparoscope, an ablation device, a surgical instrument, or an elongated tool.

3. The system of claim 1, wherein the visual imaging system is configured to calculate an insertion depth of the medical tool and at least one candidate tip location.

4. The system of claim 3, wherein the visual imaging system correctly calculates the insertion depth when at least $n/k^n$ of the optically detectable pattern is viewable by the visual imaging system, wherein each distinct element of the pattern can have k different values and the complete pattern is $k^n$ elements long.

5. The system of claim 1, wherein the visual imaging system is configured to at least one of calculate or track an insertion depth of said tip of said medical tool based on said pattern upon being detected, and wherein the pattern is based on a sequence in which each subsequence of a given minimal fraction appears only once.

6. The system of claim 5, wherein the visual imaging system correctly calculates the insertion depth when only a portion of said minimum fraction of the pattern is viewable by the visual imaging system.

7. The system of claim 1, wherein the pattern comprises one of a De Bruijn sequence or a pseudo random binary code sequence.

8. The system of claim 1, wherein the pattern is one of marked, printed, etched, or applied to the medical tool.

9. The system of claim 1, further comprising:
an attachment coupled to the medical tool.

10. The system of claim 9, wherein a distance from the attachment to the tip is calculated by the visual imaging system, and the visual imaging system is calibrated to an actual distance from the attachment to the tip.

11. The system of claim 9, wherein the attachment comprises at least one of:
a clip-on ring, wherein the clip-on ring is one of circular, oval, cylindrical, or handle shaped; or
a reflective material.

12. The system of claim 9, wherein the attachment includes the optically detectable pattern, the pattern used by the visual imaging system to calculate and track insertion depth, the pattern being initially created using a cyclic sequence in which each subsequence of a given minimal length appears only once.

13. The system of claim 1, wherein the visual imaging system further comprises:
one or more light emitting devices, the one or more light emitting devices illuminating a coating on the medical tool, the coating, in response to the illumination, producing or reflecting a light of a specific wavelength, wherein the plurality of light sensitive devices are sensitive to light of the specific wavelength.

14. The system of claim 13, wherein the coating exhibits the pattern on illumination, the pattern detectable by the visual imaging system, the pattern used by the visual imaging system to calculate and track insertion depth, the pattern being created using a cyclic sequence in which each subsequence of a given minimal length appears only once.

15. The system of claim 1, wherein the plurality of light sensitive devices comprise one or more cameras.

16. A method for image guided surgery comprising:
receiving, by one or more processors, input from one or more light-sensitive devices mounted on an imaging probe and arranged outside of a patient, the input being based on light reflected from a tool, wherein the tool includes an optically detectable non-repeating pattern extending along a sufficient portion of said tool such that at least a portion of said optically detectable non-repeating pattern remains visible outside of a patient during surgery;
detecting, by the one or more processors, the optically detectable non-repeating pattern extending along the tool based on said input from one or more light-sensitive devices;
identifying, by the one or more processors, the tool based on the optically detectable non-repeating pattern;
tracking, by the one or more processors, the tool based on the portion of said optically detectable non-repeating pattern that remains visible outside of said patient during surgery;
calculating, by the one or more processors, one or more candidate tip locations in a three dimensional space using the portion of said optically detectable non-repeating pattern that remains visible outside of said patient during surgery;
receiving, by the one or more processors, images from the imaging probe; and
displaying, by the one or more processors, output from the imaging probe and overlaying a real-time representation of the tool and an insertion depth of the tip and the one or more candidate tip locations.

17. The method of claim 16, wherein the one or more visible features minimize false-positive-detections.

18. The method of claim 16, further comprising:
determining a tool type based on the one or more visible features.

19. The method of claim 18, further comprising:
determining whether the determined tool type is suitable for a current use; and displaying one or more warnings if an inappropriate tool is used.

\* \* \* \* \*